US011833258B2

(12) United States Patent
Flieg et al.

(10) Patent No.: US 11,833,258 B2
(45) Date of Patent: Dec. 5, 2023

(54) METHOD FOR STERILIZING WATER-FILLED DEVICES

(71) Applicant: GAMBRO LUNDIA AB, Lund (SE)

(72) Inventors: Ralf Flieg, Rangendingen (DE); Wolfgang Freudemann, Hechingen (DE); Torsten Knoer, Burladingen (DE)

(73) Assignee: GAMBRO LUNDIA AB, Lund (SE)

( * ) Notice: Subject to any disclaimer, the term of this patent is extended or adjusted under 35 U.S.C. 154(b) by 712 days.

(21) Appl. No.: 16/638,671

(22) PCT Filed: Aug. 16, 2018

(86) PCT No.: PCT/EP2018/072161
§ 371 (c)(1),
(2) Date: Feb. 12, 2020

(87) PCT Pub. No.: WO2019/034714
PCT Pub. Date: Feb. 21, 2019

(65) Prior Publication Data
US 2021/0187137 A1 Jun. 24, 2021

(30) Foreign Application Priority Data
Aug. 17, 2017 (EP) .................................... 17186610

(51) Int. Cl.
*A61L 2/07* (2006.01)
*A61M 1/16* (2006.01)

(52) U.S. Cl.
CPC .............. *A61L 2/07* (2013.01); *A61M 1/1686* (2013.01); *A61L 2202/24* (2013.01)

(58) Field of Classification Search
CPC ...... A61L 2/07; A61L 2202/24; A61L 2/0064; A61M 1/1686; B65D 51/002; B65D 51/165
See application file for complete search history.

(56) References Cited

U.S. PATENT DOCUMENTS

| | | | | |
|---|---|---|---|---|
| 1,137,388 A | * | 4/1915 | Earp-Thomas | ........ C12M 45/22 435/810 |
| 2,340,102 A | * | 1/1944 | Barr | ...................... B65B 31/046 604/415 |
| 4,411,866 A | | 10/1983 | Kanno | |
| 5,961,921 A | * | 10/1999 | Addy | ...................... A61L 2/186 422/33 |
| 6,495,100 B1 | * | 12/2002 | Lin | ........................ A61L 2/208 422/33 |
| 2009/0261038 A1 | * | 10/2009 | Heim | ...................... A61M 1/36 210/257.2 |
| 2014/0315280 A1 | * | 10/2014 | Ehwald | .................. C12M 29/26 435/257.1 |

FOREIGN PATENT DOCUMENTS

| | | | | |
|---|---|---|---|---|
| CA | 2523895 C | * | 12/2013 | ............. A23L 31/00 |
| GB | 2201392 | | 9/1988 | |
| JP | S62164469 | | 7/1987 | |
| WO | WO1999/002119 | | 1/1999 | |
| WO | WO-2006073145 A1 | * | 7/2006 | ............... A23L 2/52 |

OTHER PUBLICATIONS

PCT Search Report and Written Opinion prepared for PCT/EP2018/072161, completed Aug. 28, 2018.

* cited by examiner

*Primary Examiner* — Regina M Yoo
(74) *Attorney, Agent, or Firm* — BARNES & THORNBURG LLP

(57) ABSTRACT

The present disclosure relates to a method of steam-sterilizing liquid-filled medical devices, e.g., filtration and/or diffusion devices like ultrafilters and capillary dialyzers.

10 Claims, 3 Drawing Sheets

METHOD FOR STERILIZING WATER-FILLED DEVICES

CROSS-REFERENCE TO RELATED APPLICATIONS

This application is the U.S. national phase of PCT/EP2018/072161, filed on Aug. 16, 2018, which claims the benefit of European Patent Application Serial Number 17186610.6, filed on Aug. 17, 2017, the entire disclosures of both of which are incorporated herein by reference.

TECHNICAL FIELD

The present disclosure relates to a method of steam-sterilizing liquid-filled medical devices, e.g., filtration and/or diffusion devices like ultrafilters and capillary dialyzers.

BACKGROUND OF THE INVENTION

The steam-sterilization of liquid-filled medical devices, for instance, filtration and/or diffusion devices, poses a particular challenge. The temperature increase during steam-sterilization causes a pressure increase within the closed liquid-filled device, which in turn brings about deformation of components and can cause leaks or the formation of stress cracks in the housing of the device.

It would be desirable to have a steam sterilization process which is suitable for liquid-filled medical devices.

SUMMARY

The present disclosure provides a method of steam-sterilizing a liquid-filled medical device. The process uses a cannulated stopper comprised of an elastomer to seal a fluid port of the medical device. The cannulated stopper acts as a pressure relief valve to limit over-pressure within the medical device. The stopper is self-sealing, so that no liquid leaks from the medical device at ambient pressure.

DETAILED DESCRIPTION

Figure 1:
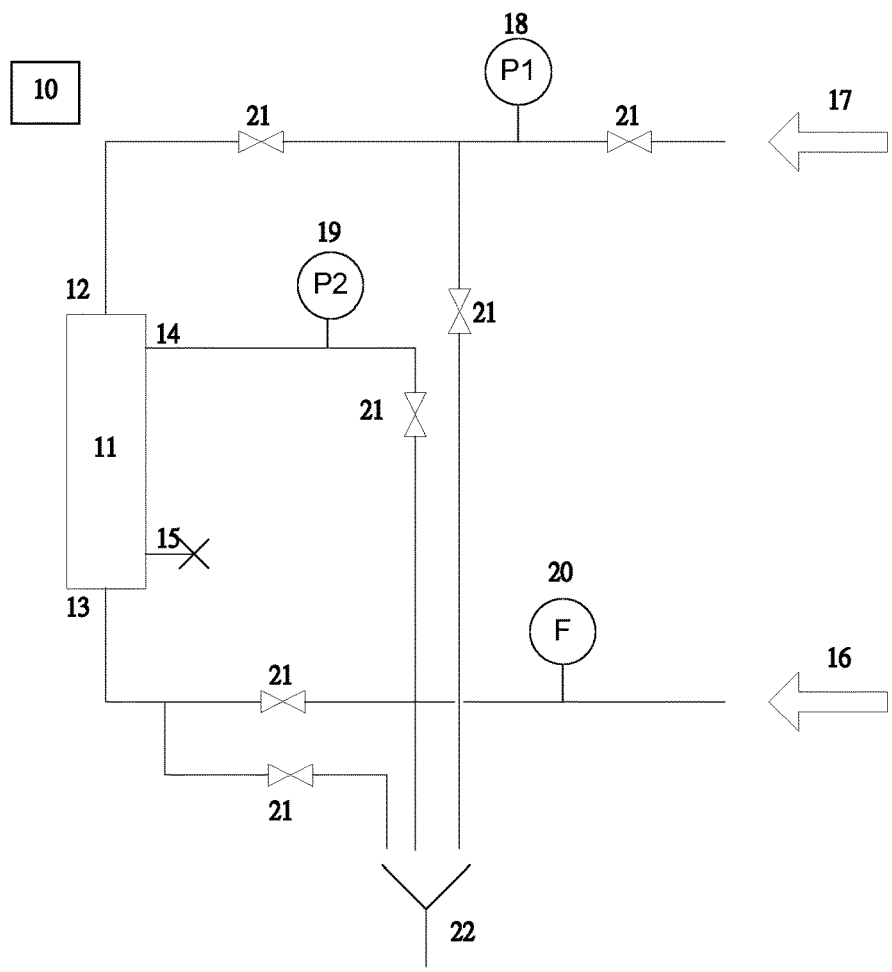
FIG. 1 is a schematic representation of two versions of a setup for measuring internal pressure of a medical device being heated.

The present disclosure provides a process for steam-sterilizing a liquid-filled medical device, e.g., a filtration and/or diffusion device, for instance, an ultra-filter or a capillary dialyzer.

The process comprises providing a liquid-filled medical device featuring at least one open liquid port. A liquid port is a port on the medical device that is configured for liquid transport into or out of the medical device, i.e., an inlet or outlet for a liquid. Usually, the liquid-filled medical device will have more than one liquid port, but most of them will be closed to prevent the liquid from flowing from the device. In one embodiment, all but one of the liquid ports of the liquid-filled medical device are closed. In another embodiment, all but two of the liquid ports of the liquid-filled medical device are closed.

At least one open liquid port of the liquid-filled medical device is closed with a cannulated stopper comprised of an elastomeric material. Any remaining open ports of the liquid-filled medical device are closed before sterilization; and the closed liquid-filled medical device then is steam-sterilized.

In one embodiment, the liquid-filled medical device is a filtration and/or diffusion device. In one embodiment, the medical device is a dialyzer, an ultrafilter, or a plasma filter, or an adsorber column, for instance, a hemocathartic column. In one embodiment, the medical device comprises hollow fiber membranes. In a further embodiment, the medical device comprises particulate material, e.g., polymer beads or carbon particles. In a particular embodiment, the liquid-filled medical device is a filtration and/or diffusion device filled with water or physiological saline and comprising hollow fiber membranes. In another particular embodiment, the medical device is a liquid-filled filtration and/or diffusion device comprising hollow fiber membranes and particulate material. In one embodiment, the particulate material is located in the space surrounding the hollow fiber membranes.

The liquid-filled medical device features at least one liquid port. In one embodiment, the liquid-filled medical device features a plurality of liquid ports, e.g., two, three or four liquid ports.

In one embodiment, the liquid-filled medical device comprises two compartments separated by a semipermeable membrane, and at least one of the two compartments features an inlet port and an outlet port for a liquid, e.g., blood. In a further embodiment, both compartments each feature an inlet port and an outlet port for a liquid. In another embodiment, one of the compartments only has an inlet port for a liquid. In another embodiment, one of the compartments does not feature liquid ports; or only ports which have been permanently sealed. In one embodiment, the liquid ports are connectors of a filtration and/or diffusion device for hemofiltration, hemodiafiltration, or hemodialysis, as described in DIN EN ISO 8637 (2014).

In the process of the present disclosure, the opening of at least one liquid port of the medical device to be steam-sterilized is closed with a cannulated stopper. In one embodiment, the opening of the port is closed by inserting a cannulated stopper into the opening of the port. In one embodiment, the stopper has a conical shape, its minimum diameter being smaller than the diameter of the opening of the port and its maximum diameter being larger than the diameter of the opening of the port. After insertion, part of the plug protrudes from the opening of the port. In another embodiment, the stopper features a section of cylindrical or conical shape, the maximum diameter of this section being smaller than or equal to the inner diameter of the port; and a head section having a diameter which is equal to or larger than the outer diameter of the port. After insertion, the head section of the plug covers the opening and the rim of the port.

The cannulated stopper is comprised of an elastomeric material. Examples of suitable elastomeric materials include silicone rubber, natural rubber (NR), butadiene rubber (BR), chloroprene rubber (CR), butyl rubber (IIR), styrene-butadiene rubber (SBR), nitrile rubber (NBR), ethylene propylene diene rubber (EPDM), and polyurethane elastomers. In one embodiment, the stopper is comprised of a silicone rubber. In one embodiment, the stopper has been produced by injection molding.

The cannulated stopper features a cannulation extending from the top of the stopper to its bottom and providing a through conduit from the interior of the liquid-filled medical device to the outside when the cannulation is in an expanded state. At ambient pressure, the cannulation is closed by the elastic restoring force of the elastomeric material. In one embodiment, the cannulation is produced by piercing a stopper comprised of an elastomeric material with a cannula having an outer diameter in the range of from 0.4 to 1.0 mm, for instance, 0.6 to 0.8 mm.

In case the medical device to be steam-sterilized comprises more than one liquid port, all liquid ports have to be closed before sterilizing the device. In one embodiment, all but one liquid port are closed by non-cannulated stoppers. In another embodiment, two or more of the liquid ports are closed by cannulated stoppers. It is generally sufficient to use a cannulated stopper in only one of the liquid ports of the medical device. However, for medical devices having two compartments separated by a semipermeable membrane, it may be advantageous to use a cannulated stopper in one liquid port of each compartment.

After all liquid ports of the liquid-filled medical device have been closed, the opening of at least one liquid port having been closed with a cannulated stopper, the liquid-filled medical device is steam-sterilized. Steam sterilization is a procedure well known in the art, and the person skilled in the art is familiar with the equipment and parameters to be used. In one embodiment, the medical device is sterilized with steam at a temperature in the range of from 119 to 121° C. for a time period of at least 20 minutes.

The present disclosure also is directed to the use of a cannulated stopper comprised of an elastomeric material in the steam-sterilization of a liquid-filled medical device. In one embodiment, the elastomeric material comprises silicone rubber. In one embodiment, the cannulation in the cannulated stopper has been produced by piercing a non-cannulated stopper with a cannula having an outer diameter in the range of from 0.4 to 1.0 mm, in particular, from 0.6 to 0.8 mm.

In one embodiment, the medical device is a filtration and/or diffusion device comprising hollow fiber membranes. In a further embodiment, the medical device comprises particulate material located in the space surrounding the hollow fiber membranes.

EXAMPLES

FIG. 1 shows two versions a) and b) of a setup for measuring internal pressure of a medical device being heated. In both versions of the setup, a filtration and/or diffusion device 11, for instance, a dialyzer, having a lower blood port 12, an upper blood port 13, a lower dialysate port 14, and an upper dialysate port 15 is present. Lower blood port 12 is sealed by a stopper 16. Lower dialysate port 14 has been welded shut. Upper dialysate port 15 is connected to a pressure gauge 18 which indicates the pressure P within the device 11. Upper blood port 13 is closed by cannulated stopper 17. The device 11 is partially immersed into a heated bath 19 that is used to control the temperature within the device 11. The second version of the setup (FIG. 1b) additionally comprises a syringe 20 connected to the cannulation of stopper 17. The syringe 20 allows collecting and measuring liquid emerging from the device 11.

Figure 2:
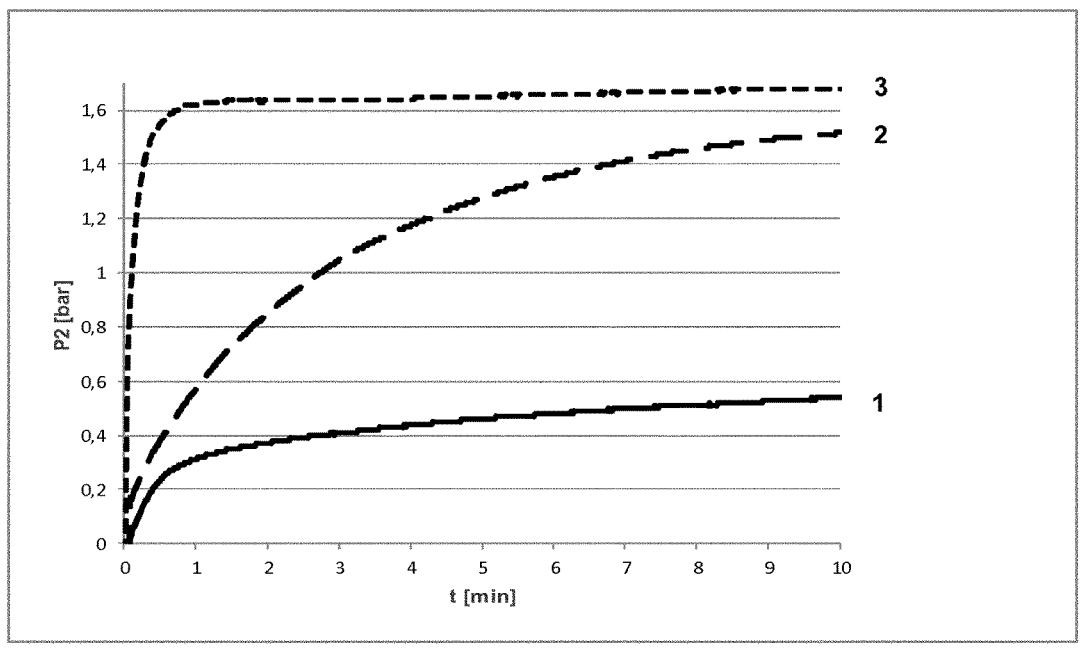
FIG. 2-FIG. 6 show several pressure curves obtained during heating experiments.

Stoppers 16 comprised of silicone rubber were produced by injection molding of a two-component liquid silicone rubber (ELASTOSIL® LR 3003/60 A/B, Wacker Chemie AG, D-81737 Munich). The design of the stoppers 16 is shown in FIG. 2. After 5 min at 165° C. in the mold and 4 hours of post-curing at 200° C. in ventilated air, the material has a density of 1.13 g/cm$^3$ (ISO 1183-1 A), and a hardness of 60 Shore A (DIN 53505). It has a viscosity, measured according to DIN 53019 at a shear rate of 0.9 s$^{-1}$, of 1,100,000 mPa·s. Its tensile strength is 9.40 N/mm$^2$ and the elongation at break is 340% (both measured according to DIN 53504 S 1). The material shows a rebound resilience of 67%, measured according to DIN 53512.

Comparative Example 1

A medical device 11 comprising hollow fiber membranes having a surface area of 2.3 m$^2$ with lower dialysate port 14 welded shut was filled with water, blood ports 12 and 13 were closed with stoppers 16; and upper dialysate port 15 was connected to a pressure gauge 18. The device 11 was immersed into a water bath 19 kept at a temperature of (80±2)° C. and the pressure P inside the device 11 was monitored.

Figure 3:
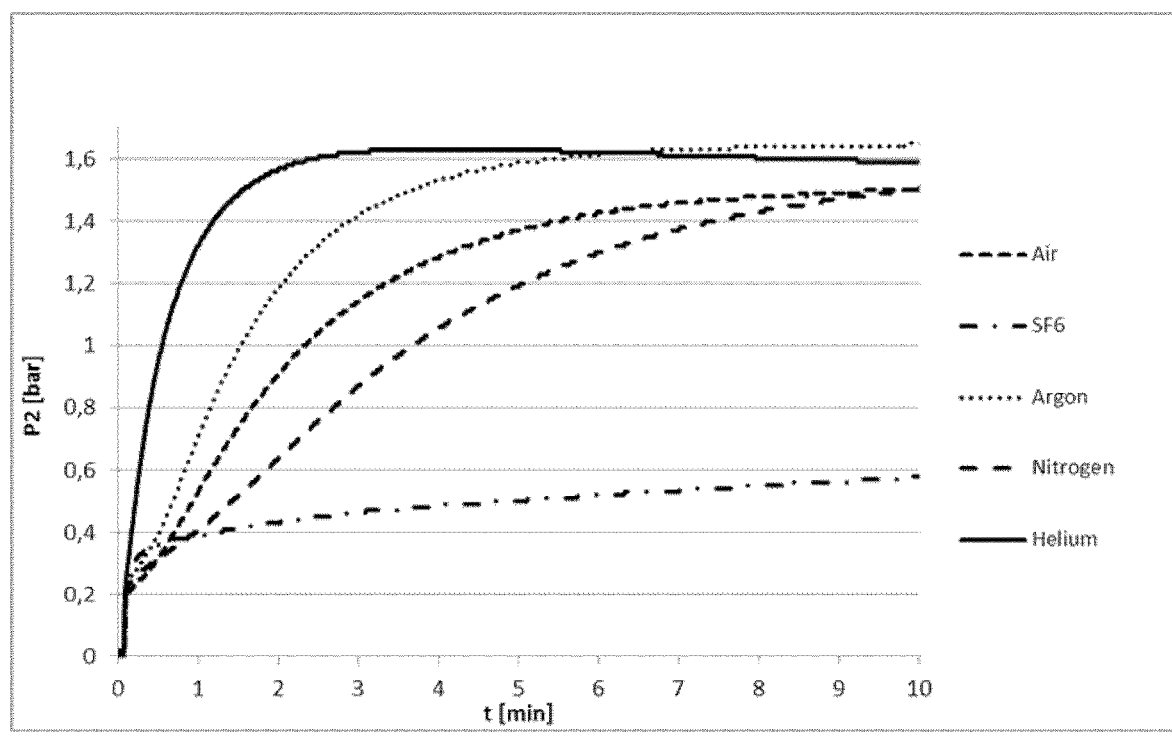
Figure 4:
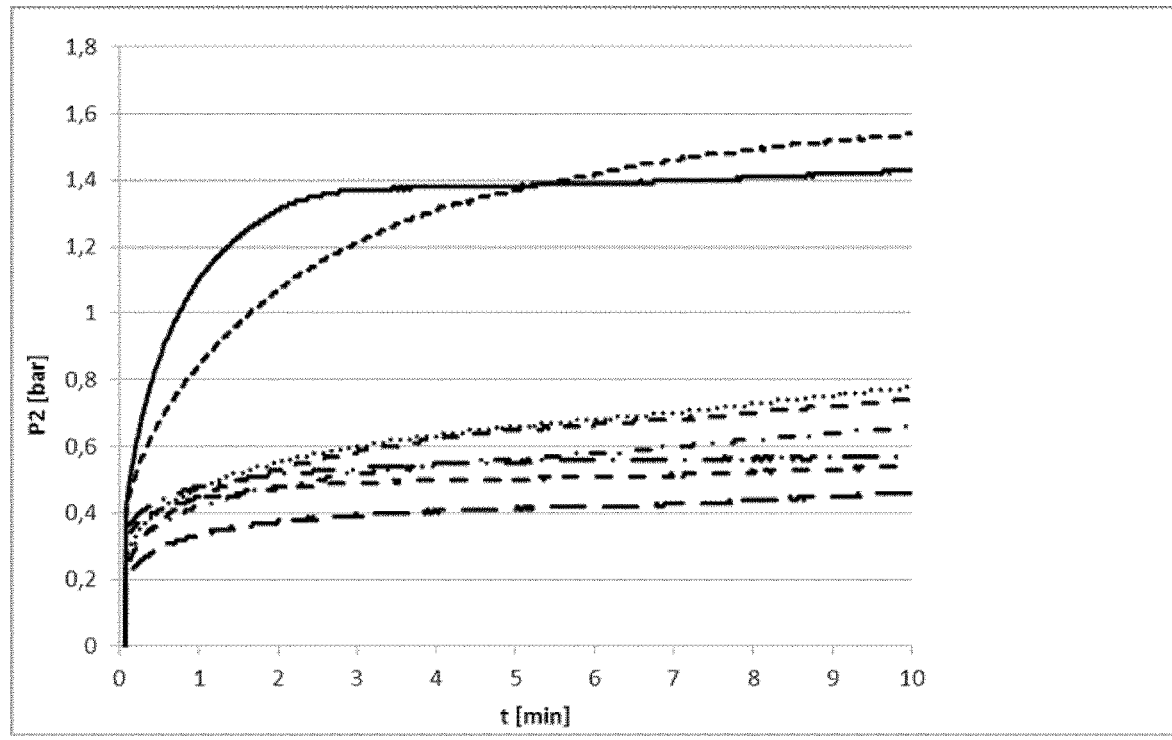
Figure 5:
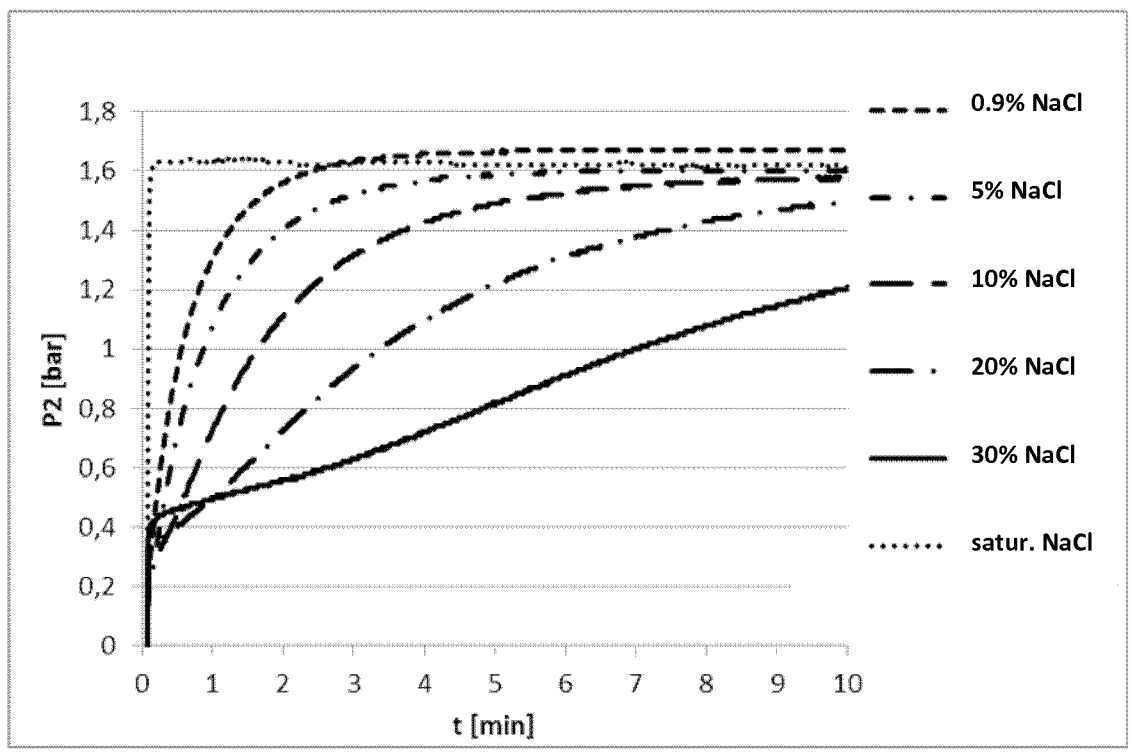
Figure 6:
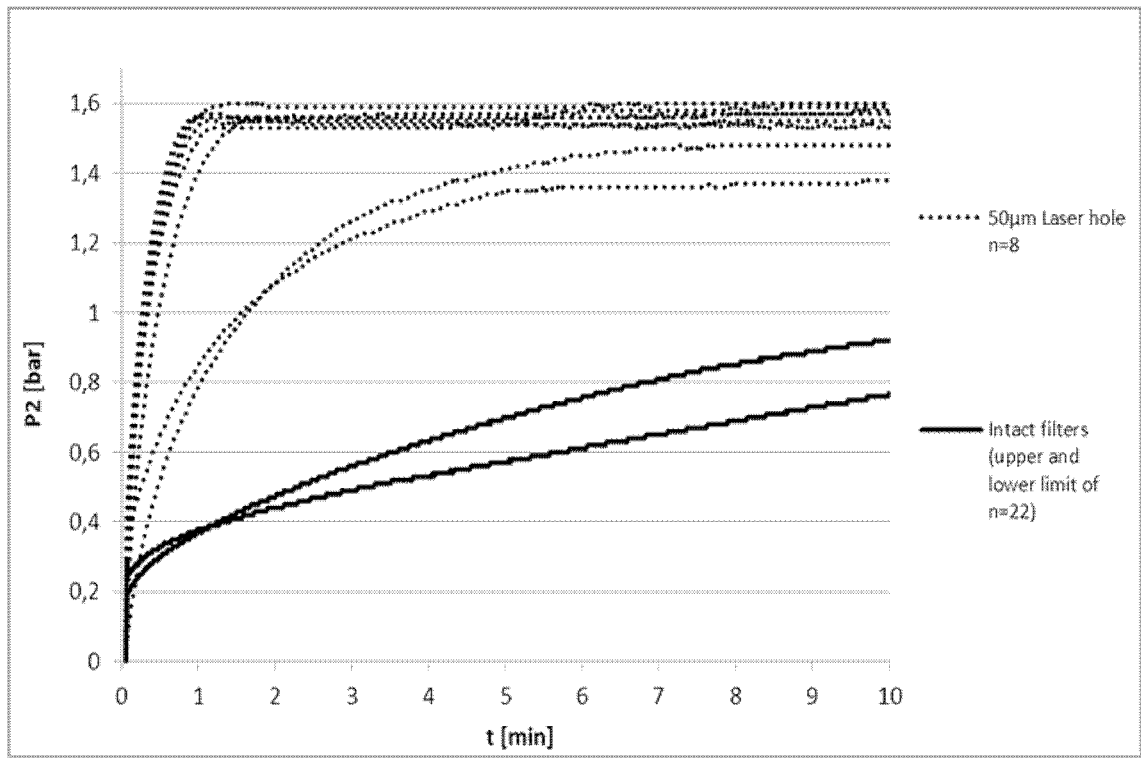

The resulting pressure curve (pressure P over time t) is shown in FIG. 3 (curve 1). After immersion of the device 11, the pressure P inside the device 11 quickly rose to values exceeding 2 bar (g). When the pressure P had reached 3.9 bar (g), the experiment was stopped. No water had leaked from the device 11.

Example 2

A stopper 16 comprised of silicone rubber was pierced with a cannula having an outer diameter of 0.45 mm to produce a cannulated stopper 17.

A medical device 11 comprising hollow fiber membranes having a surface area of 2.3 m$^2$ and lower dialysate port 14 welded shut was filled with water, lower blood port 12 was closed with a stopper 16, upper blood port 13 was closed with the cannulated stopper 17; and upper dialysate port 15 was connected to a pressure gauge 18. The device 11 was immersed into a water bath 19 kept at a temperature of (80±2)° C. and the pressure P inside the device 11 was monitored (Setup according to FIG. 1a).

The resulting pressure curve is shown in FIG. 3 (curve 2). After immersion of the device 11, the pressure P inside the device 11 rose to a maximum of 1.59 bar (g) and then tapered off. At the end of the experiment, the pressure P was 1.17 bar (g), and 7.5 g of water had leaked from the device.

Example 3

A stopper 16 comprised of silicone rubber was pierced with a cannula having an outer diameter of 0.60 mm to produce a cannulated stopper 17.

A medical device 11 comprising hollow fiber membranes having a surface area of 2.3 m$^2$ and lower dialysate port 14 welded shut was filled with water, lower blood port 12 was closed with a stopper 16, upper blood port 13 was closed with the cannulated stopper 17; and upper dialysate port 15 was connected to a pressure gauge 18. The device 11 was immersed into a water bath 19 kept at a temperature of (80±2)° C. and the pressure P inside the device 11 was monitored (Setup according to FIG. 1a).

The resulting pressure curve is shown in FIG. 3 (curve 3). After immersion of the device 11, the pressure P inside the device 11 rose to a maximum of 1.50 bar (g) and then tapered off. At the end of the experiment, the pressure P was 1.26 bar (g), and 7.0 g of water had leaked from the device.

Example 4

A stopper 16 comprised of silicone rubber was pierced with a cannula having an outer diameter of 0.80 mm to produce a cannulated stopper 17.

A medical device 11 comprising hollow fiber membranes having a surface area of 2.3 m² and lower dialysate port 14 welded shut was filled with water, lower blood port 12 was closed with a stopper 16, upper blood port 13 was closed with the cannulated stopper 17; and upper dialysate port 15 was connected to a pressure gauge 18. The device 11 was immersed into a water bath 19 kept at a temperature of (80±2)° C. and the pressure P inside the device 11 was monitored (Setup according to FIG. 1a).

The resulting pressure curve is shown in FIG. 3 (curve 4). After immersion of the device 11, the pressure P inside the device 11 rose to a maximum of 1.15 bar (g) and then tapered off. At the end of the experiment, the pressure P was 0.5 bar (g), and 6.5 g of water had leaked from the device.

Example 5

A stopper 16 comprised of silicone rubber was pierced with a cannula having an outer diameter of 0.90 mm to produce a cannulated stopper 17.

A medical device 11 comprising hollow fiber membranes having a surface area of 2.3 m² and lower dialysate port 14 welded shut was filled with water, lower blood port 12 was closed with a stopper 16, upper blood port 13 was closed with the cannulated stopper 17; and upper dialysate port 15 was connected to a pressure gauge 18. The device 11 was immersed into a water bath 19 kept at a temperature of (80±2)° C. and the pressure P inside the device 11 was monitored (Setup according to FIG. 1a).

The resulting pressure curve is shown in FIG. 3 (curve 5). After immersion of the device 11, the pressure P inside the device 11 rose to a maximum of 0.08 bar (g) and then tapered off. At the end of the experiment, the pressure P was 0.0 bar (g), and 7.5 g of water had leaked from the device.

Example 6

A stopper 16 comprised of silicone rubber was pierced with a cannula having an outer diameter of 0.45 mm to produce a cannulated stopper 17.

A medical device 11 comprising hollow fiber membranes having a surface area of 2.3 m² and polymer beads in the space surrounding the hollow fiber membranes was used for the experiment. The lower dialysate port 14 of the device 11 had been welded shut. The device 11 was filled with water, lower blood port 12 was closed with a stopper 16, upper blood port 13 was closed with the cannulated stopper 17; and upper dialysate port 15 was connected to a pressure gauge 18. The device 11 was immersed into a water bath 19 kept at a temperature of (80±2)° C. and the pressure P inside the device 11 was monitored (Setup according to FIG. 1a).

The resulting pressure curve is shown in FIG. 3 (curve 6). After immersion of the device 11, the pressure P inside the device 11 rose to a maximum of 1.8 bar (g) and then tapered off. At the end of the experiment, the pressure P was 1.05 bar (g), and 5.6 g of water had leaked from the device.

Example 7

A stopper 16 comprised of silicone rubber was pierced with a cannula having an outer diameter of 0.45 mm to produce a cannulated stopper 17. A 30 ml syringe 20 was connected to the cannula which had a length of 10 mm.

A medical device 11 comprising hollow fiber membranes having a surface area of 2.3 m² and lower dialysate port 14 welded shut was filled with water, lower blood port 12 was closed with a stopper 16, upper blood port 13 was closed with the cannulated stopper 17 connected to the syringe 20; and upper dialysate port 15 was connected to a pressure gauge 18. The device 11 was immersed into a water bath 19 kept at a temperature of (80±2)° C. and the pressure P inside the device 11 was monitored (Setup according to FIG. 1b).

The resulting pressure curve is shown in FIG. 3 (curve 7). The maximum of the pressure P inside the device 11 reached during the experiment was 0.18 bar (g). The plunger of the syringe began to move when the pressure P reached 0.05 bar (g). During the experiment, a maximum volume of 7.5 ml water was displaced into the syringe 20. After removing the water bath 19 and cooling the device to room temperature, a residual volume of 1 ml remained in the syringe 20.

LIST OF REFERENCE SIGNS

10 Testing setup
11 filter
12 lower blood port
13 upper blood port
14 lower dialysate port
15 upper dialysate port
16 stopper
17 cannulated stopper
18 pressure gauge
19 heated bath
20 syringe
P pressure

The invention claimed is:

1. A process for steam-sterilizing a liquid-filled medical device, the process comprising the steps of: closing at least one open liquid port of the liquid-filled medical device with a stopper; closing any remaining open ports of the liquid-filled medical device; and steam-sterilizing the closed liquid-filled medical device, characterized in that the stopper is obtainable by piercing a non-cannulated stopper comprised of an elastomeric material with a cannula having an outer diameter in the range of from about 0.4 mm to about 1.0 mm, wherein the liquid-filled medical device is a filtration device.

2. The process of claim 1, wherein the filtration device is a dialyzer.

3. The process of claim 1, wherein the elastomeric material comprises silicone rubber.

4. The process of claim 1, wherein the outer diameter the cannula is in the range of from about 0.6 mm to about 0.8 mm.

5. The process of claim 1, wherein the filtration device is filled with water or physiological saline, and wherein the filtration device comprises hollow fiber membranes.

6. The process of claim 1, wherein the filtration device comprises hollow fiber membranes and particulate material.

7. The process of claim 6, wherein the particulate material is located in a space surrounding the hollow fiber membranes.

8. The process of claim 6, wherein the particulate material comprises polymer beads, carbon particles, or a combination thereof.

9. The process of claim 1, wherein the elastomeric material is selected from the group consisting of silicone rubber, natural rubber (NR), butadiene rubber (BR), chloroprene rubber (CR), butyl rubber (IIR), styrene-butadiene rubber (SBR), nitrile rubber (NBR), ethylene propylene diene rubber (EPDM), a polyurethane elastomer, and any combination thereof.

10. The process of claim 1, wherein the liquid-filled medical device is sterilized with steam at a temperature in the range of from about 119° C. to about 121° C. for a time period of at least 20 minutes.

* * * * *